United States Patent [19]

Hagiwara

[11] Patent Number: 5,174,293
[45] Date of Patent: Dec. 29, 1992

[54] MEDICAL APPARATUS INCLUDING ON ISOLATING TRANSFORMER APPARATUS FOR ISOLATING MEDICAL APPARATUS FROM NON-MEDICAL APPARATUS TO PREVENT ELECTRICAL SHOCKS TO PATIENTS

[75] Inventor: Toshihiko Hagiwara, Tokyo, Japan

[73] Assignee: Olympus Optical Co., Ltd., Tokyo, Japan

[21] Appl. No.: 730,517

[22] Filed: Jul. 12, 1991

Related U.S. Application Data

[63] Continuation of Ser. No. 427,861, Oct. 26, 1989.

[30] Foreign Application Priority Data

Nov. 17, 1988 [JP] Japan .......................... 63-150071[U]
Jul. 17, 1989 [JP] Japan .................... 1-182593

[51] Int. Cl.⁵ ...................... A61B 5/05; H01R 13/639
[52] U.S. Cl. ................................ 128/653.1; 128/908; 439/373; 439/304; 439/345; 439/371; 361/394; 361/427
[58] Field of Search .................... 174/135; 336/107; 361/392, 393, 394, 395, 427, 428, 429; 248/500, 505, 510; 439/304, 345, 367, 368, 369, 371, 372, 373; 128/908, 653.1; 606/34, 35

[56] References Cited

U.S. PATENT DOCUMENTS

| 2,728,058 | 12/1955 | Phalen | 439/371 |
| 3,163,481 | 12/1964 | Salvader | 439/371 |
| 3,811,104 | 5/1974 | Caldwell | 439/373 |
| 4,577,187 | 3/1986 | Barr et al. | 248/917 |
| 4,658,298 | 4/1987 | Takeda et al. | |
| 4,662,697 | 5/1987 | Moses | 439/373 |

FOREIGN PATENT DOCUMENTS

| 1084602 | 8/1980 | Canada | 439/373 |
| 3000115 | 7/1981 | Fed. Rep. of Germany | 439/345 |
| 0083083 | 4/1920 | Switzerland | 439/373 |

OTHER PUBLICATIONS

IBM Technical Disclosure Bulletin, vol. 28, No. 7, Dec., 1985, pp. 2785-2798, FIG. 10A, 10B, 11, and 12.

Primary Examiner—Leo P. Picard
Assistant Examiner—Michael W. Phillips
Attorney, Agent, or Firm—Frishauf, Holtz, Goodman & Woodward

[57] ABSTRACT

A medical apparatus comprises an electrical medical apparatus for use with an endoscope connectable thereto and adapted for at least one a diagnostic and medical treatment; at least one electrical non-medical apparatus including a line cord and a plug, which is used in association with the electrical medical apparatus; and an isolating transformer apparatus isolating a patient from electrical shocks from the electrical medical apparatus used together with the electrical non-medical apparatus. The isolating transformer apparatus is connectable by an authorized person to a commercial power supply and is connected to the line cord and plug of the electrical non-medical apparatus. The electrical medical apparatus is connectable to the commerical power supply. The isolating transformer apparatus includes a housing having a plurality of walls; a transformer contained in the housing, the transformer having a primary winding which is connectable to the commercial power supply, and a secondary winding which is electrically isolated from the primary winding; and a power supply socket mounted on a wall of the housing and being connected to the secondary winding, the socket receiving the plug of the electrical non-medical apparatus. The isolating transformer apparatus also has a retainer provided on an outside portion of the housing for preventing the plug of the electrical non-medical apparatus from being removed from the power supply socket, and a lock device for locking the retainer for preventing removal of the retainer without an engaging and disengaging tool.

13 Claims, 14 Drawing Sheets

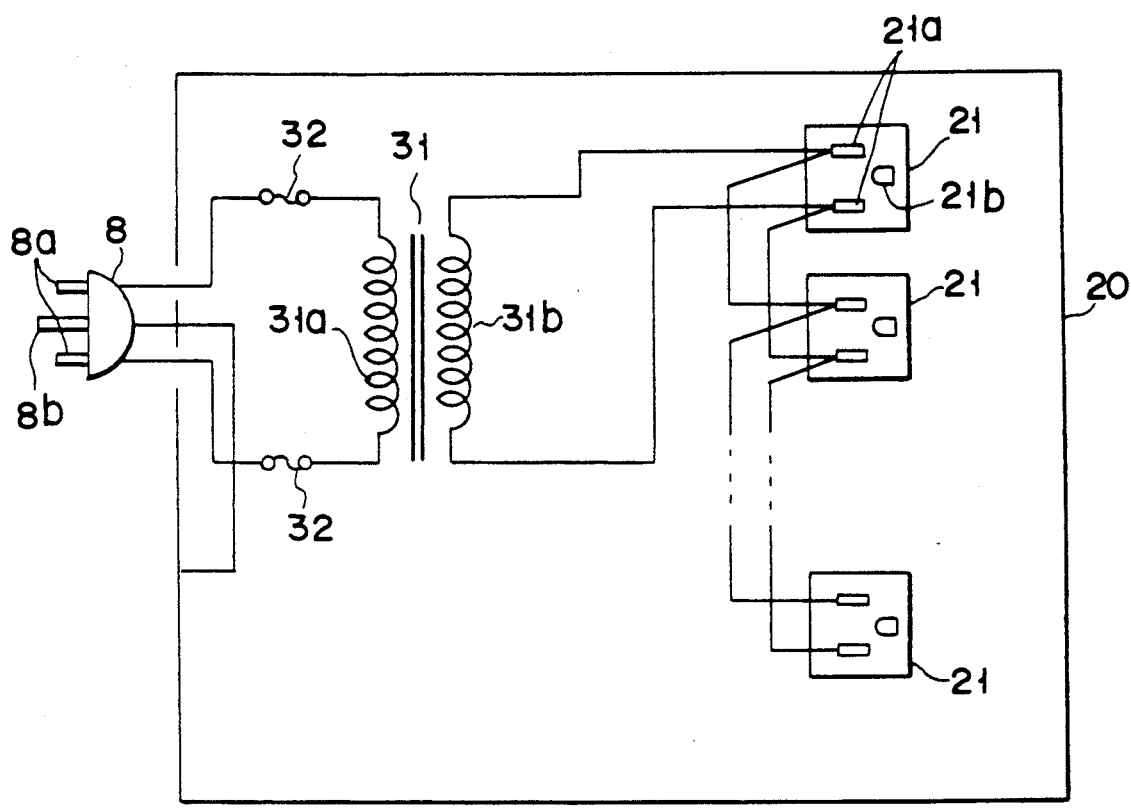
F I G. 4

MEDICAL APPARATUS INCLUDING ON ISOLATING TRANSFORMER APPARATUS FOR ISOLATING MEDICAL APPARATUS FROM NON-MEDICAL APPARATUS TO PREVENT ELECTRICAL SHOCKS TO PATIENTS

This application is a continuation of application Ser. No. 427,861, filed Oct. 26, 1989 now abandoned.

BACKGROUND OF THE INVENTION

1. Field of the Invention

The present invention relates to an insulating (isolating) transformer apparatus for ensuring safety against a leakage current of an electric device.

2. Description of the Related Art

Recently, medical systems have been widely employed in the field of medical treatment. These systems can have a plurality of medical electric devices (hereinafter, referred to as "ME device"), rather than a single ME device, which are combined, or a single ME device can be combined with other general electric devices.

Regarding the ME device, safety standards for leakage current (not a functional current, i.e., an unintentionally produced current) have been established and countermeasures thereto have been devised, in order to protect a patient against an electric shock caused when a doctor or an assistant touches the ME device and the patient.

Such safety standards or countermeasures, however, are not provided for general electric devices other than the ME devices. Thus, a leakage current higher than an allowable value defined in the safety standards for ME device may occur in a general electric device, which may endanger a patient.

Under these circumstances, an isolating transformer apparatus, as described below, has conventionally been connected between a commercial power source and a general electric device, thereby reducing leakage current from the general electric device.

The conventional transformer apparatus comprises a transformer, which includes a primary winding connected to the commercial power source and a secondary winding insulated from the primary winding, and a power source socket connected to the secondary winding of the transformer. A power source plug of a general electric device is connected to the power source socket.

In the case of the conventional isolating transformer apparatus, there is a concern that a user may erroneously pull out the power source plug of the electric device from the isolating transformer apparatus, and may connect it to a wall socket (i.e., a socket for medical use connected to the commercial power source).

In such a case, a leakage current higher than the allowable value may occur in the general electric device, and a patient may suffer an electric shock through a doctor or an assistant who has touched the ME device, as mentioned above.

SUMMARY OF THE INVENTION

An object of the present invention is to provide a safe isolating transformer apparatus wherein a power source plug of a general electric device, other than an ME (medical electric) device, is prevented from being disconnected from a socket of the transformer apparatus, thus avoiding the danger of electric shock due to leakage current from the general electric device.

According to one aspect of the present invention, a plug locking means for an isolating transformer apparatus comprises a housing, a transformer contained in the housing, the transformer having a primary winding connected to the commercial power source and a secondary winding isolated from the primary winding, a power source socket, connected to the secondary winding of the transformer, having an exposed surface exposed to the outside of the housing and an insertion hole to which the power source plug is inserted, a retainer removably mounted on an outside of the housing, for preventing removal of the power source plug from the power source socket once the plug is connected to the socket, and a fixing member for removably fixing the retainer to the housing, the fixing member being disengaged only by using a disengaging tool.

The retainer can forcibly prevent the plug from being disconnected from the socket. The plug can be disconnected from the socket only by taking out the fixing member from the housing with use of the disengaging tool, and removing the retainer from the housing. Unless the retainer is taken out of the housing, the plug cannot be disconnected from the socket. Thus, a danger of electric shock due to leakage current from the general electric device can be surely avoided, and the safety can be ensured.

According to another aspect of the present invention, the plug retaining means for an isolating transformer apparatus comprises a housing, a transformer contained in the housing, the transformer having a primary winding connected to the commercial power source and a secondary winding isolated from the primary winding, a power source socket, connected to the secondary winding of the transformer, having an exposed surface exposed to the outside of the housing and an insertion hole to which the power source plug of a general electric device, a retainer provided on the power source socket, the stopper engages the plug to prevent the removal of the plug from the socket when the plug is inserted into the socket, release member for releasing the engagement of the retainer and the power source plug, and release preventing member for holding the release member in its non-operable state, the release preventing member being removed only by use of a disengaging tool.

The release preventing means holds the release member in its non-operable state, thereby preventing the plug from being disconnected from the socket. By taking out the fixing member from the housing with use of the disengaging tool, and removing the release preventing member from the housing, the release member is set in the operable state so that the plug can be disconnected from the socket. Unless the release preventing member is taken out of the housing, the plug cannot be disconnected from the socket. Thus, a danger of electric shock due to leakage current from the general electric device can be avoided, and the safety can be ensured.

BRIEF DESCRIPTION OF THE DRAWINGS

FIG. 4 schematically shows a circuit structure within the isolating transformer apparatus of FIG. 1;

DETAILED DESCRIPTION OF THE PREFERRED EMBODIMENTS

The preferred embodiments of the present invention will be described with reference to the accompanying drawings.

Figure 1:
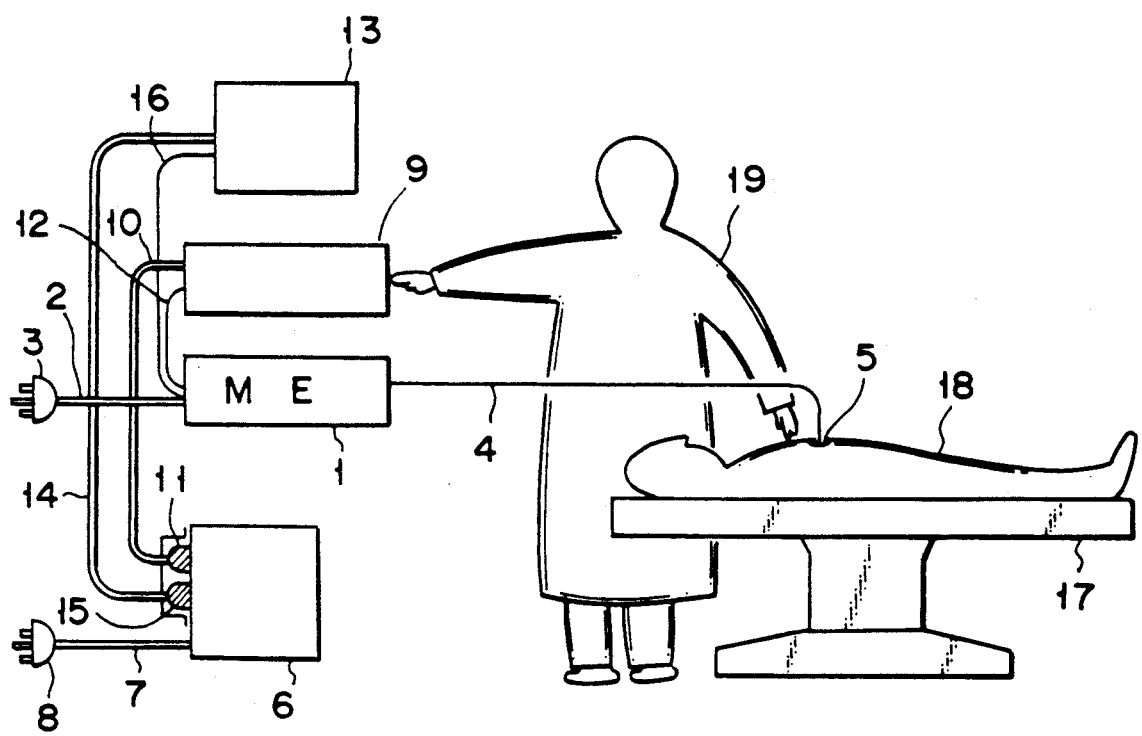
FIG. 1 schematically shows a structure of an isolating transformer apparatus and a peripheral section thereof according to a first embodiment of the present invention.

In FIG. 1, an ME (medical electric) device 1 has a power source cord 2 and a power source plug 3. The plug 3 is connected to a wall socket (a socket for medical use connected to a commercial power source) to obtain electric power for the ME device 1. One end of a lead wire 4 is connected to the ME device 1. The other end of the lead wire 4 is provided with a patient electrode 5.

An isolating transformer apparatus 6 according to the first embodiment of the present invention has a power source cord 7 and a power source plug 8. The plug 8 is also connected to the wall socket (a socket for medical use connected to a commercial power source). The isolating transformer apparatus 6 also has power source sockets to which power source plugs of general electric devices are connected.

A general electric device (e.g., a recording device) 9 has a power source cord 10 and a power source plug 11. The plug 11 is connected to the socket of the isolating transformer apparatus 6, so that power is supplied to the electric device 9 from the transformer 6. One end of a signal line 12 is connected to the electric device 9, and the other end of the line 12 is connected to the ME device 1.

Another general electric device (e.g., a TV monitor) 13 has a power source cord 14 and a power source plug 15. The plug 15 is connected to the socket of the isolating transformer apparatus 6, so that power is supplied to the electric device 13 from the transformer 6. One end of a signal line 16 is connected to the electric device 13, and the other end of the line 16 is connected to the ME device 1.

A patient 18 is laid on a bed 17. The patient electrode 5 of the ME device 1 is attached to the patient 18 by an operator 19 who controls the general electric devices 9 and 13.

Figure 2:
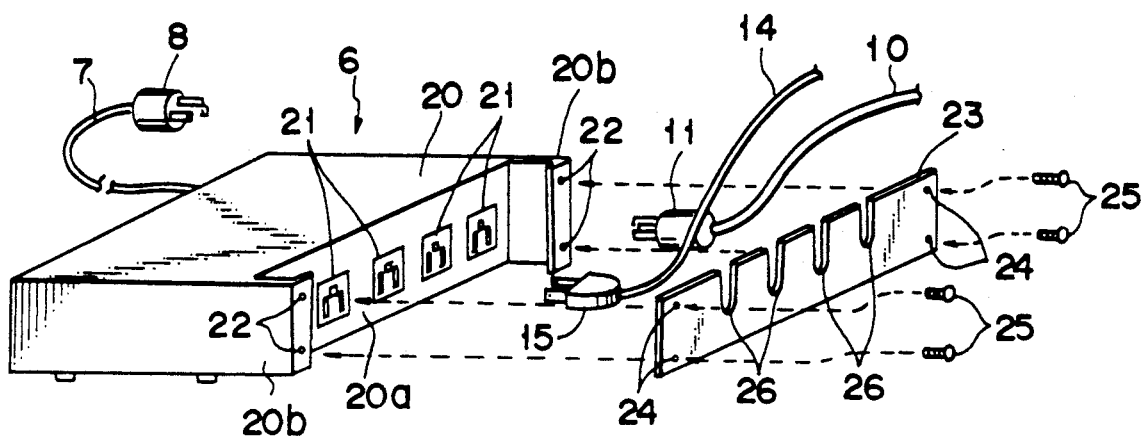
FIG. 2 is a perspective view showing the isolating transformer apparatus of FIG. 1 from which power source plugs of general electric devices are disconnected.
Figure 3:
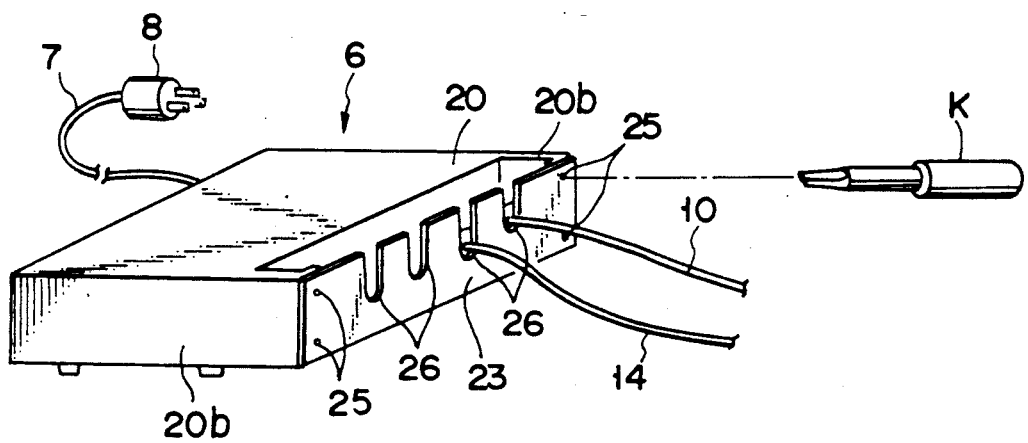
FIG. 3 is a perspective view showing the isolating transformer apparatus of FIG. 1 to which the power source plugs of the general electric devices are connected.

A specific structure of the insulating transformer apparatus 6 will now be described with reference to FIGS. 2, 3 and 4.

Sockets 21 are provided on a front panel (or a rear panel) 20a of a casing 20 of the insulating transformer apparatus 6. Front end portions of side plates 20b of the casing 20 are projected from the front panel 20a and are bent inward substantially at right angles. The bent portions of the side plates 20b have tapped holes 22.

The plugs 11 and 15 of general electric devices 9 and 13 are connected to the sockets 21. In the state wherein the plugs 11 and 15 are connected to the sockets 21, a retainer 23 is mounted on the bent portions of the side plates 20b. The retainer 23 has screw holes 24. Screws as an example of fixing means 25 are passed through the screw holes 24 and are engaged in the tap holes 22 of casing 20 by means of a disengaging tool K such as a screwdriver. Thus, the retainer 23 is fixed on the casing 20 by the screws 25.

U-shaped notches 26 are formed in the retainer 23 at locations corresponding to the sockets 21. The width of each notch 26 is greater than the diameter of the cord 10 or 14 so that the notch 26 may allow the cord 10 or 14 to be inserted therein. However, the width of each notch 26 is smaller than that of each plug 11 or 15 so that the notch 26 may prevent the plug 11 or 15 from being drawn through the notch 26. A bottom portion of each notch 26 is rounded.

As shown in FIG. 4, a power source plug 8 of the isolating transformer apparatus 6 has two power source pins 8a and one protective ground pin 8b. The ground pin 8b is connected to the casing 20.

A transformer 31 is disposed in the casing 20. The transformer 31 has a primary winding 31a and a secondary winding 31b insulated from the primary winding 31a. Both ends of the primary winding 31a are connected to the power source pins 8a of plug 8 through fuses 32. Both ends of the secondary winding 31b are connected to a pair of terminals 21a of each socket 21.

Each socket 21 has, in addition to the terminals 21a, a protective ground terminal 21b corresponding to the power source plug 3 of the ME device 1.

The operation of the isolating transformer apparatus 6 having the above-described structure will now be described.

First the plugs 11 and 15 of electric devices 9 and 13 are connected to the sockets 21 of the isolating transformer apparatus 6. Then, the retainer 23 is mounted on the casing 20 of the apparatus 6, and is fixed by means of the screws 25.

The power source plug 8 of the apparatus 6 is connected to the wall socket.

In this state, the electric devices 9 and 13 are supplied with electric, power through the transformer 31.

With the isolating transformer apparatus 6 being provided between the commercial power source and the electric devices 9 and 13, the level of a leakage current of the electric devices 9 and 13 can be reduced substantially to the level of a leakage current of the ME device. Thus, even if the operator 19 touches these electric devices 9 or 13, the patient 18 suffers no electric shock.

The retainer 23 has the U-shaped notches 26 at locations corresponding to the sockets 21 arranged on the front panel 20a of casing 20. The size of each notch 26 is determined so as to allow free passage of only the power source cord 10 or 14, and to prevent each plug 11 or 15 from being pulled out through the notch 26. Thus, once the stopper 23 is fixed on the casing 20, the plugs 11 and 15 can not be pulled out from the sockets 21. Further, since the stopper 23 is fixed on the casing 20 by means of the screws 25, the stopper 23 cannot be removed from the casing 20 unless the screws 25 are disengaged by using the d tool K such as the screwdriver. Since the retainer 23 prevents the removal of the plugs 11 and 15 from sockets 21 of transformer 6, a user can be prevented from mistakingly pulling the plugs 11 and 15 connect them to the wall sockets. Consequently, a danger of electric shock due to a leakage current from the electric devices 9 and 13 can be completely eliminated, and safety can be ensured.

If only a service engineer or the like of the ME device is permitted to connect the plugs 11 and 15 of electric devices 9 and 13 to the isolating transformer apparatus 6 and to fixedly mount the retainer 23 on the casing 6, and a manual of the transformer apparatus 6 describes that it is inhibited for the user to remove the screws by using the disengaging tool K, the safety can be ensured perfectly.

In other words, the fixing of the retainer 23 cannot be released unless the screws 25 are removed by the disengaging tool K. Even if the user stumbles on the cord 10 or 14, the plug 11 or 15 is not disconnected, and safety is maintained.

Figure 5:
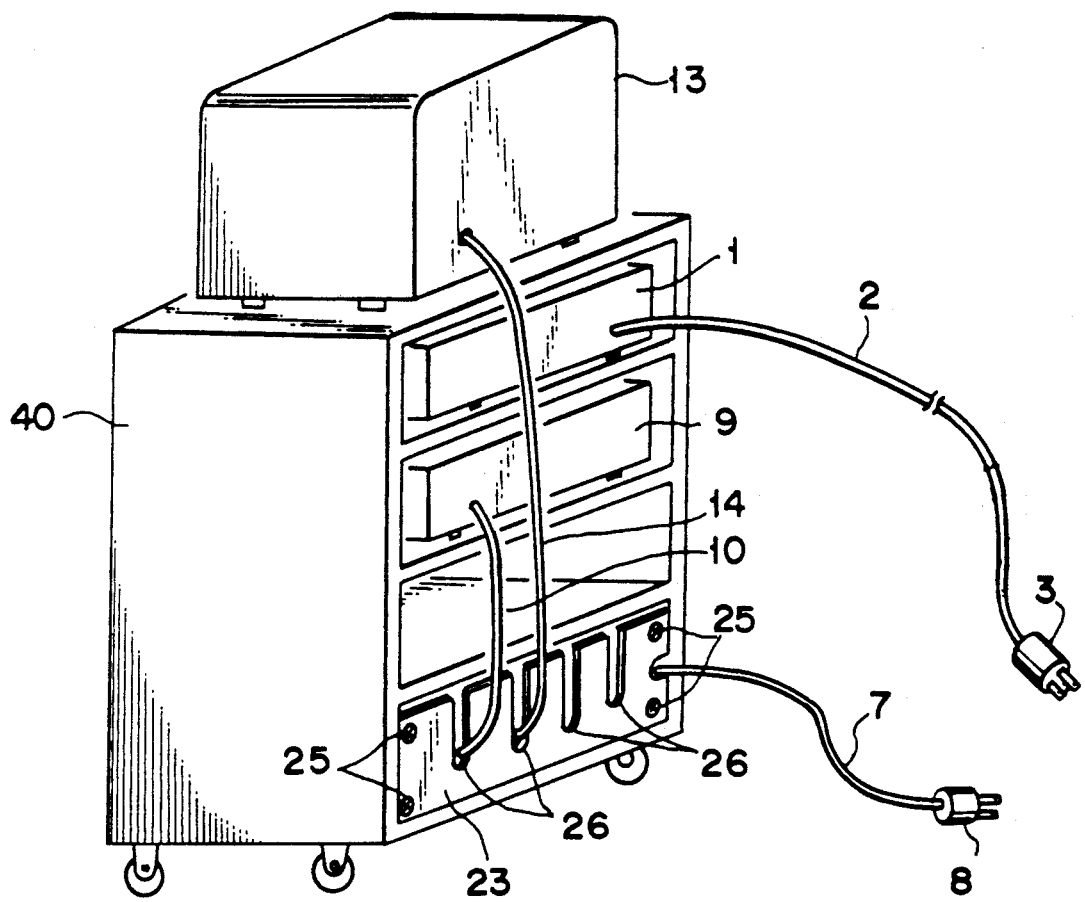
FIG. 5 is a perspective view of a modification of the first embodiment.

As shown in FIG. 5, the ME device 1 and electric devices 9 and 13 of the above embodiment may be mounted on a cart 40, so that these devices may be moved together one body. In this case, the retainer 23 may be attached on the rear portion of cart 40 which contains the transformer 6.

In the above embodiment, the protective ground terminal 21b of each sockets 21 may be connected to the casing 20. In this case, when a plurality of ME devices 1 are respectively connected to the sockets 21, a bias voltage of each ME device becomes equal, and safety can be further ensured.

Figure 6:
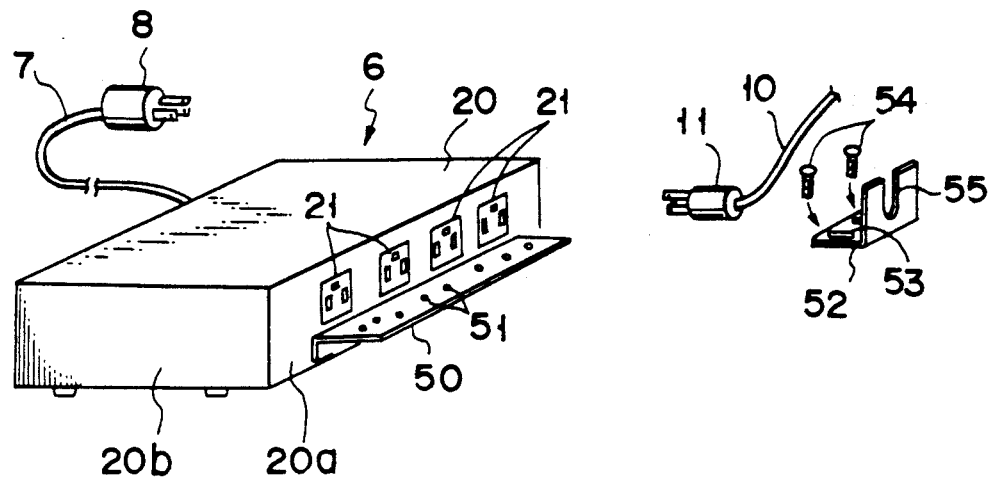
FIG. 6 is a perspective view showing the isolating transformer apparatus according to a second embodiment of the present invention from which power source plugs of the general electric devices are disconnected.
Figure 7:
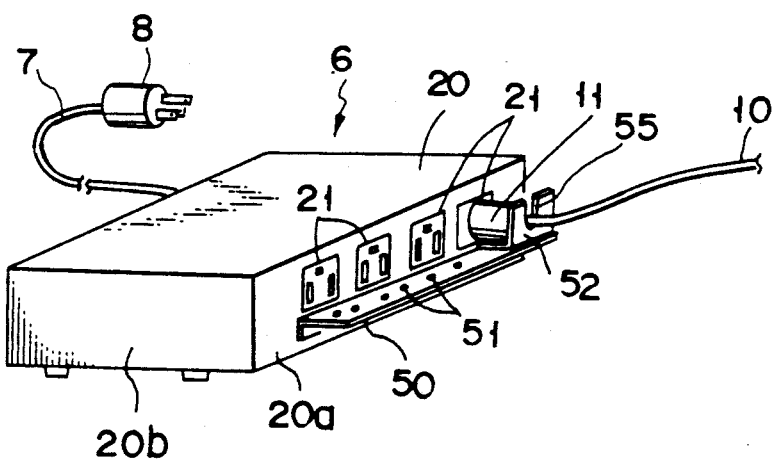
FIG. 7 is a perspective view showing the isolating transformer apparatus of FIG. 6 to which the power source plugs of the general electric devices are connected.

A second embodiment of the present invention will now be described with reference to FIGS. 6 and 7.

In this embodiment, the side plates 20b of the casing 20 are not projected from the front panel 20a, unlike in the first embodiment. Instead, an L-shaped flange 50 is directly attached on the front panel 20a at a position lower than each sockets 21. Tapped holes 51 are formed in the flange 50. A plurality of L-shaped removable retainers 52 are attached on the flange 50.

A pair of elongated holes 53 are formed in a bottom portion of each retainer 52. Screws or fixing means 54 are inserted into the screw holes 53. After the screws 54 have been passed through the screw holes 53, the screws 54 are engaged in the holes 51 of the flange 50 by means of the disengaging tool K such as the driver. Each retainer 52 is fixed on the flange 50 by the screws 54.

A U-shaped notch 55 is formed in a vertical portion of each retainer 52. The width of the notch 55 is greater than the diameter of the cord 10 or 14 so that the cord 10 or 14 may pass through the notch 55. However, the width of the notch 55 is smaller than that of the plug 11 or 15 so that the plug 11 or 15 may not pass through the notch 55.

A bottom edge of each notch 55 is rounded.

The number of retainers 52 is equal to the number of sockets 21.

The flange 50 and retainer 52 constitute retainer means for preventing the plugs 11 and 15 from pulled out of the sockets 21 of the isolating transformer apparatus, thereby completely eliminating a danger of electric shock due to a leakage current from the general electric device 9 or 13.

Since each screw hole 53 of the retainer 52 has an elongated shape, a distance between the vertical portion of retainer 52 and the sockets 21 can be adjusted depending on the size of plug 11 or 15. Thus, the plugs 11 or 15 of various sizes may be employed, and the plugs can be closely connected to the sockets 21. As a result, imperfect contact of the plug 11 or 15 can be prevented.

Figure 8:
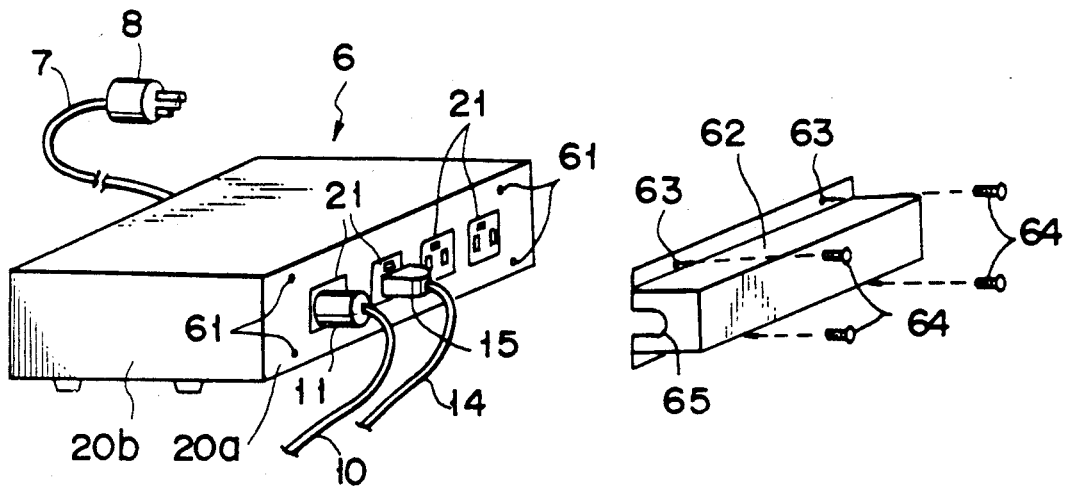
FIG. 8 is a perspective view showing the isolating transformer apparatus according to a third embodiment of the present invention from which power source plugs of the general electric devices are disconnected.
Figure 9:
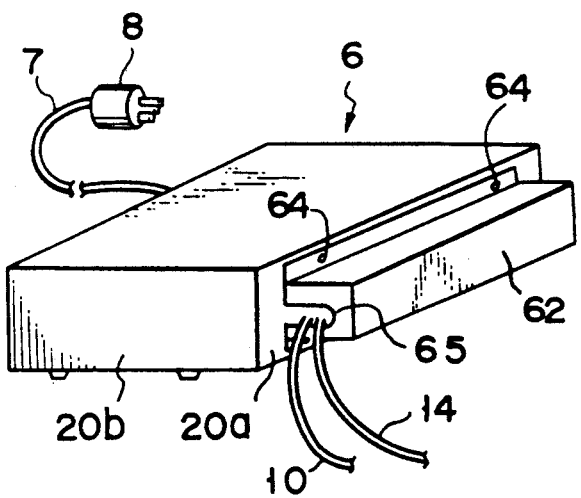
FIG. 9 is a perspective view showing the isolating transformer apparatus of FIG. 8 to which the power source plugs of the general electric devices are connected.

FIGS. 8 and 9 show a third embodiment of the present invention.

In the third embodiment, the front panel 20a of the casing 20 has tapped holes 61 at four corners thereof. A box-shaped removable retainer 62 is attached to the front panel 20a. Flange portions are provided on the peripheral edges of the retainer 62. Four screw holes 63 are formed in the flange portions. Screws (fixing means) 64 are inserted into each screw hole 63. After being passed through the screw hole 63, the screw 64 is engaged in the tapped hole 61 in the casing 20. The retainer 62 is fixed on the front panel 20a by means of the screws 64.

The retainer 62 has a U-shaped notch 65 at its side. The cords 10 and 14 are passed through the notch 65.

According to the third embodiment, the stopper 62 prevents the plugs 11 and 15 from being pulled out of the sockets 21 of the isolating transformer apparatus 6. Also, a danger of electric shock due to a leakage current of electric device 9 or 13 can surely be avoided.

Regarding the second and third embodiments, the ME device and general electric devices can also be mounted on the cart, as shown in FIG. 5.

FIGS. 10 to 17 show a fourth embodiment of the present invention.

Figure 10:
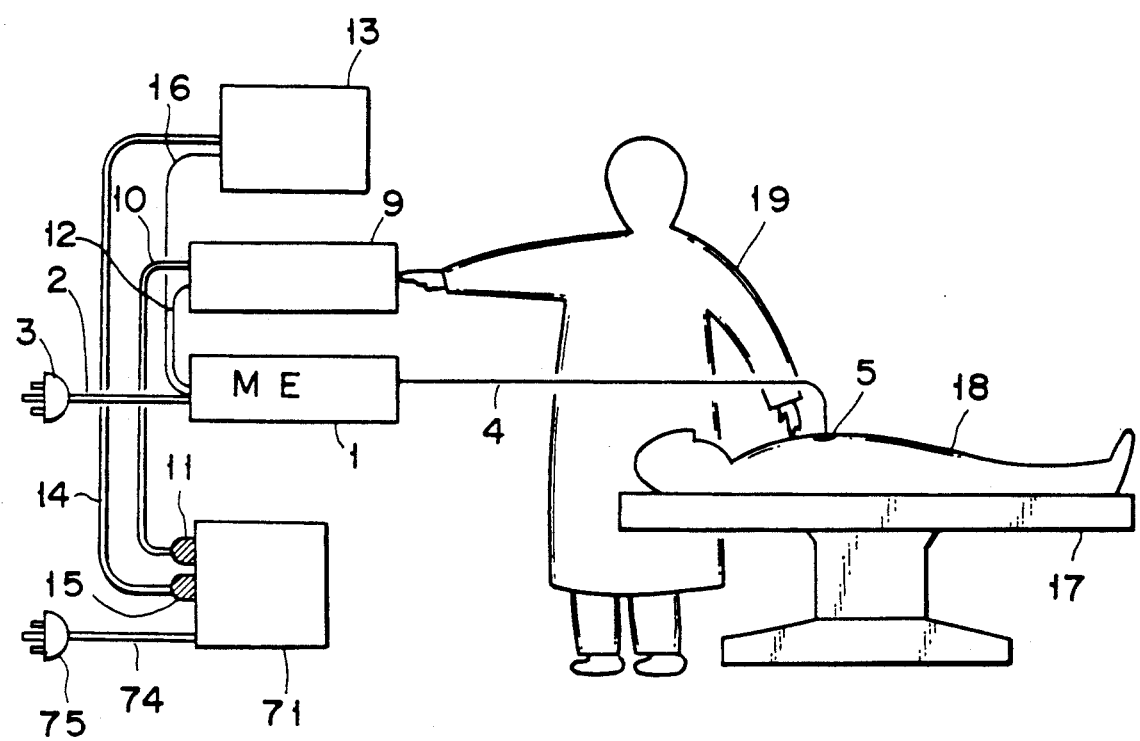
FIG. 10 schematically shows a structure of an isolating transformer apparatus and a peripheral section thereof according to a fourth embodiment of the present invention.
Figure 11:
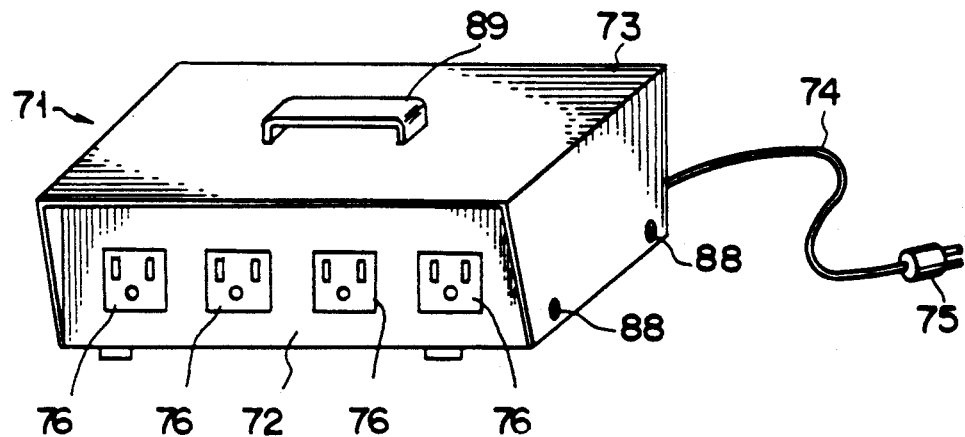
FIG. 11 is a perspective view showing an outer appearance of the isolating transformer apparatus of FIG. 10.
Figure 12:
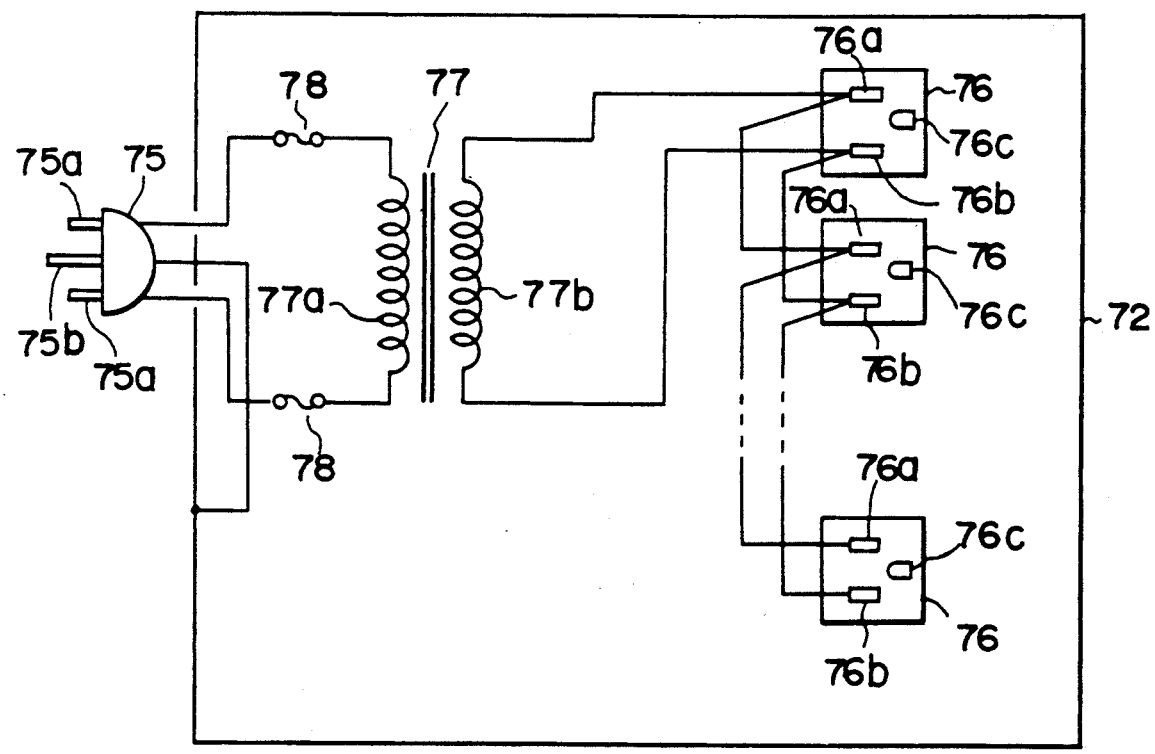
FIG. 12 shows a schematic circuit structure within the isolating transformer apparatus of FIG. 10.
Figure 13:
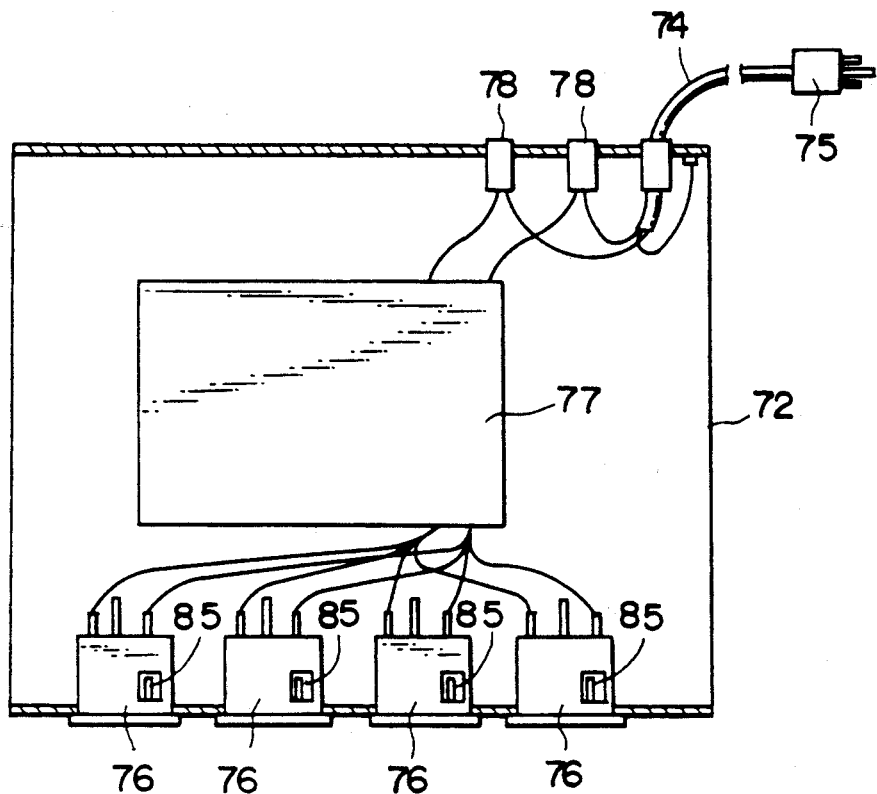
FIG. 13 is a transverse cross-sectional view showing an internal structure of the isolating transformer apparatus of FIG. 10.

FIG. 10 shows a structure of an isolating transformer apparatus 71 and its peripheral section of the fourth embodiment. FIG. 11 shows an outer appearance of the isolating transformer apparatus 71. FIG. 12 shows an electric circuit within the isolating transformer apparatus 71, and FIG. 13 shows an internal structure of the insulating transformer apparatus 71. The transformer apparatus 71 has a casing 72 having an opening at its top or its sides. The top opening or side openings of the casing 72 are closed by a cover (release-prevention means) 73.

The isolating transformer apparatus 71 has a power source cord 74 and a power source plug 75. The plug 75 is connected to a wall socket (a socket for medical use connected to a commercial power source). The plug 75 has two power source pins 75a and one protective ground pin 75b, as shown in FIG. 12. The protective ground pin 75b is connected to the casing 72.

A front panel of the casing 72 has sockets 76 for receiving the power source plug 11 of the electric device 9 (e.g., a recording device) and the power source plug 15 of the electric device 13 (e.g., a TV monitor). Each socket 76 has a pair of power source-side terminals 76a and 76b and a protective ground-side terminal 76c.

A transformer 77 is mounted in the casing 72 of the isolating transformer apparatus 71. The transformer 77 comprises a primary winding 77a and a secondary winding 77b insulated from the primary winding 77a. Both ends of the primary winding 77a are connected to the power source pins 75a of plug 75 through fuses 78. On the other hand, both ends of the secondary winding 77b are connected to the power source-side connection sections 76a and 76b of socket 76.

Figure 14:
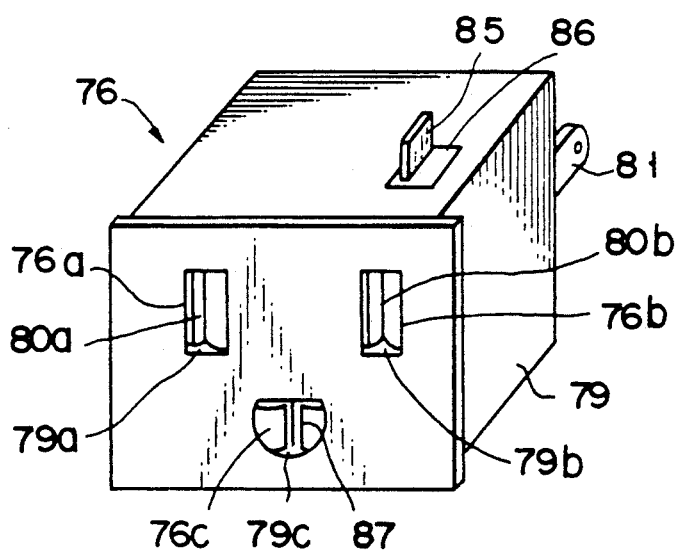
FIG. 14 is a perspective view showing a power source socket of the isolating transformer apparatus FIG. 10.
Figure 15:
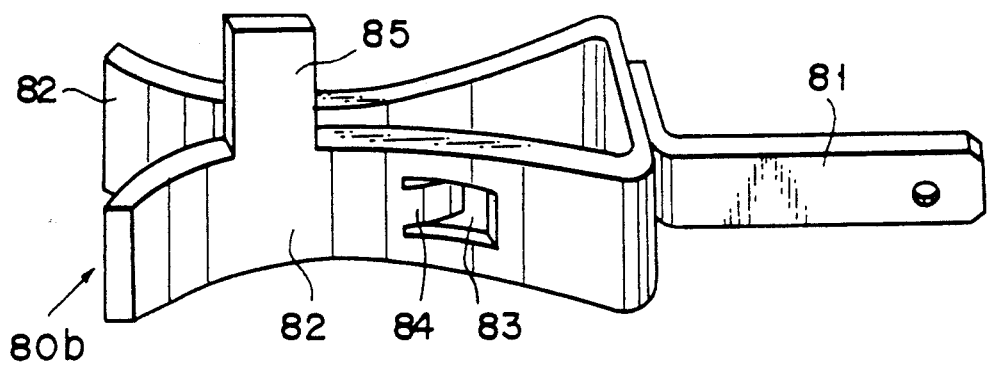
FIG. 15 is a perspective view showing a power source contact of the power source socket of FIG. 14.

As shown in FIG. 14, each power source socket 76 has an integrally molded holder 79 made of an insulating material. A pair of power source contact mounting holes 79a and 79b and a protective ground contact mounting hole 79c are formed in a front surface of the holder 79. Each of the power source-side connection sections 76a and 76b of socket 76 comprises a power source contact 80a or 80b mounted in the power source contact mounting hole 79a or 79b of each holder 79, and a terminal 81 connected to the contact 80a or 80b. As shown in FIG. 15, each contact 80a or 80b includes a pair of bent clamp portions 82 formed from leaf spring members. A common proximal end portion of the clamp portions 82 is welded to the terminal 81.

Figure 16:
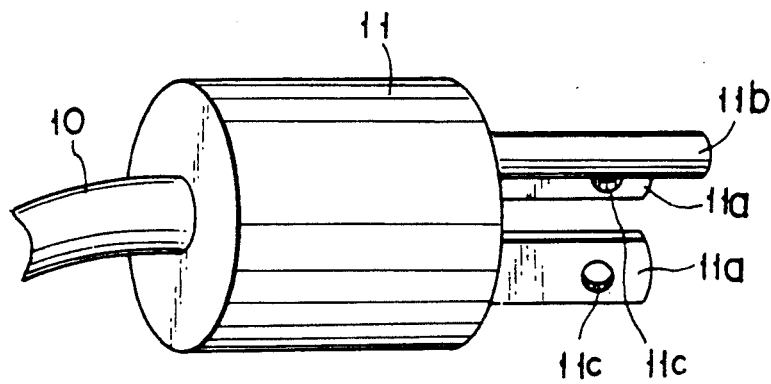
FIG. 16 is a perspective view showing a power source plug general electric device of FIG. 10.

FIG. 16 shows the plug 11 of the general electric device 9. The plug 11 has a pair of power source pins 11a and a protective ground pin 11b. Though FIG. 16 shows the plug 11 of electric device 9 representatively, the plug 15 of electric device 13 also has a pair of power source pins 15a and a protective ground pin 15b similarly. In general, a distal end portion of each pin 11a or 15a has a hole 11c or 15c for preventing the plug 11 or 15 being drawn from the corresponding socket.

The power source pins 11a or 15a of plug 11 or 15 of electric device 9 or 13 are removably fitted in the contacts 80a and 80b of the socket 76. In this manner, the plugs 11 and 15 are connected to the sockets 76.

The contact 80b of each socket 76 has disengagement prevention means for preventing disengagement of the plug 11 or 15 of electric device 9 or 13 and socket 76. The disengagement prevention means is formed, as shown in FIG. 15. Namely, a substantially U-shaped notch 83 is formed in one of clamp portions 82 of contact 80b. An inner portion defined by the notch 83 is bent toward the other clamp portion 82 to form a claw 84. A distal end of the claw 84, compared to a proximal end thereof, is located closer to the common connection portion of the clamp portions 82.

Figure 17:
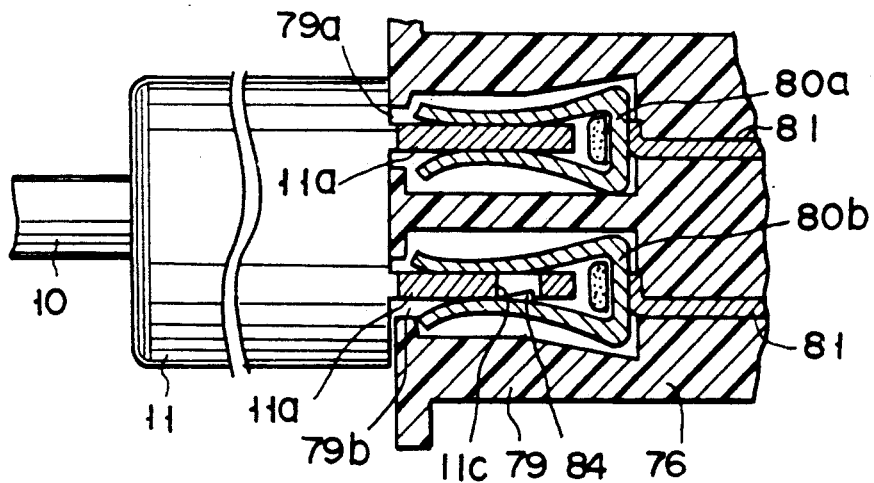
FIG. 17 is a transverse cross-sectional view illustrating the connection between the power source socket of FIG. 14 and the power source plug of FIG. 16.

An operation lever (release means) 85 is attached to the upper edge of the clamp portion 82 having the disengagement prevention means. The operation lever 85 projects from an operation lever insertion hole 8 formed in a top surface of holder 79 of socket 76. When the plug 11 or 15 of electric device 9 or 13 is connected to the corresponding socket 76, the paired pins 11a or 15a of the plug 11 or 15 are inserted between the corresponding pairs of clamp portions 82 of contacts 80a and 80b, and the protective ground pin 11b or 15b of the plug 11 or 15 is inserted into a protective ground contact 87 mounted in the protective ground contact mounting hole 79c of socket 76. In this case, as shown in FIG. 17, when the plug 11 or 15 is inserted to a predetermined point in the corresponding socket, the claw 84 of contact 80b enters the hole 11c or 15c of the pin 11a or 15a.

When the pin 11a or 15a is inserted between the corresponding pair of clamp portions 82 of contact 80b of socket 76, the claw 84 of contact 80b is deformed outwardly by the pin 11a or 15a. Thus, the pin 11a or 15a can be smoothly inserted between the clamp portions 82, and therefore the plug 11 or 15 can be inserted to a predetermined point in the socket 76.

Once the plug 11 or 15 is inserted to the predetermined position, the claw 84 enters the hole 11c or 15c of pin 11a or 15a by virtue of its own restoring force, so that the claw is engaged with the pin 11a or 15a. In this state, the pin 11a or 15a cannot be pulled out of the socket 76 and the plug 11 or 15 is prevented from being disconnected from the socket 76, since the claw 84 is engaged with the pin 11a or 15a.

If the operation lever 85 is moved to the right (in FIG. 14) in the state that the plug 11 or 15 is inserted into the socket 76 at the predetermined position and the claw 84 is engaged with the pin 11a or 15a, the clamp portion 82 having the claw 84 is elastically deformed outwardly away from the other clamp portion 82. In accordance with the elastic deformation of the clamp portion 82, the claw 84 is disengaged from the pin 11a or 15a, thereby enabling the plug 11 or 15 to be pulled out of the socket 76.

The cover 73 is attached to the casing 72 of the isolating transformer apparatus 71 by means of screws 88. In the state wherein the cover 73 is attached to the casing 72, the operation lever 85 of each socket 76 is arranged under the cover 73. In other words, the cover 73 prevents the operation lever 85 from being exposed to the outside. A handle 89 is disposed on an upper surface of the cover 73.

The operation of the isolating transformer apparatus 73 according to the fourth embodiment will now be described.

The plug 11 of electric device 9 (or plug 15 of electric device 13) is connected to the corresponding socket 76 of the insulating transformer apparatus 71. The plug 11 and the plug 15 are connected to the corresponding sockets 76 in the same manner. In this description, the connection of the plug 11 is described representatively. The plug 11 is connected to the corresponding socket 76 such that the paired pins 11a are inserted into the corresponding pairs of clamp portions 82 of the contacts 80a and 80b of socket 76, and the protective ground pin 11b of plug 11 is inserted into the protective ground pin contact 87 of socket 76. When the pin 11a is inserted, the claw 84 of the contact 80b is elastically deformed outward, i.e., away from the facing clamp portion 82. Thus, the plug 11 can be smoothly inserted into the socket 76 to the a predetermined position.

Once the plug 11 is inserted into the socket 76 to the predetermined position, the claw 84 enters the hole 11c of the pin 11a by virtue of its own restoring force, so that the claw 84 can be engaged with the pin 11a. In this state, since the claw 84 is engaged with the pin 11a, the pin 11a cannot be pulled out of the socket 76, and therefore the plug 11 cannot be disconnected from the socket 76. Since the cover 73 is attached to the casing 72 of insulating transformer apparatus 71 by means of screws 88, the operation lever 85 of each socket 76 is arranged under the cover 73. The cover 73 prevents the operation lever 85 of each socket 76 from being exposed to the outside. Thus, once the plug 11 is inserted into the socket 76 to the predetermined position, and the claw 84 of clamp portion 82 of contact 80b is engaged in the hole 11c of pin 11a, the operation lever 85 of socket 76 cannot be touched unless the screws 88 are removed by the disengaging tool K to separate the cover 73 from the casing 72. The provision of the cover 73 can prevent such a dangerous situation from occurring wherein a user pulls out the plug 11 from the socket 76 and connects it to the wall socket. A danger of electric shock due to leakage current from general electric device 9 or 13 can be surely avoided, and safety can be ensured.

When the plug 11 is disconnected from the socket 76, the cover 73 is separated from the casing 72 by taking off the screws 88 by means of the disengaging tool K. In this state, the operation lever 85 of socket 76 is moved to the right (in FIG. 14), to elastically deform the clamp portion 82 having the claw 84 in a direction away from the mating clamp portion 82. In accordance with the elastic deformation of the clamp portion 82, the claw 84 is moved out of the hole 11c or 15c of the pin 11a or 15a, thereby disengaging the claw 84 from the pin 11a or 15a. Thus, the plug 11 or 15 can be pulled out of the socket 76.

Figure 18:
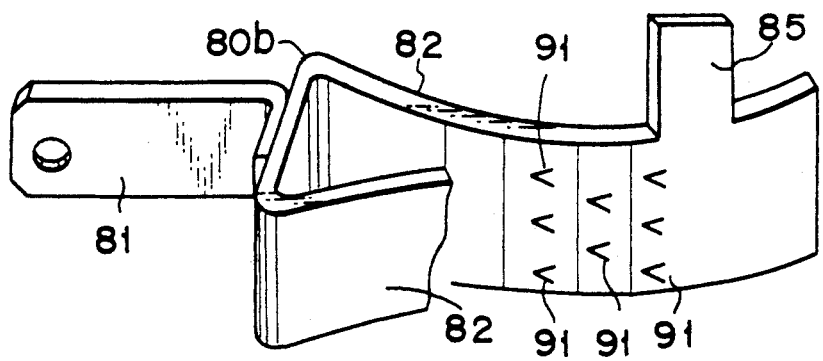
FIG. 18 is a perspective view showing a structure of a modification of the fourth embodiment.

In the fourth embodiment, the substantially U-shaped notch 83 is formed in one of clamp portions 82 of contact 80b of socket 76. The inner portion defined by the notch 83 is bent inward to form the claw 84. However, as shown in FIG. 18, it is possible to provide triangular claws 91 on the clamp portion 82, which cause no substantial frictional resistance in the direction of insertion of the pin 11a or 15a but are caught in holes 11c or 15c of the pin 11a or 15a in the direction of pull-out of the pin 11a or 15a. It is also possible to mount a cap of insulating material on the operation lever 85 of socket 76, thereby preventing a user from directly touching the contact 80b.

Figure 19:
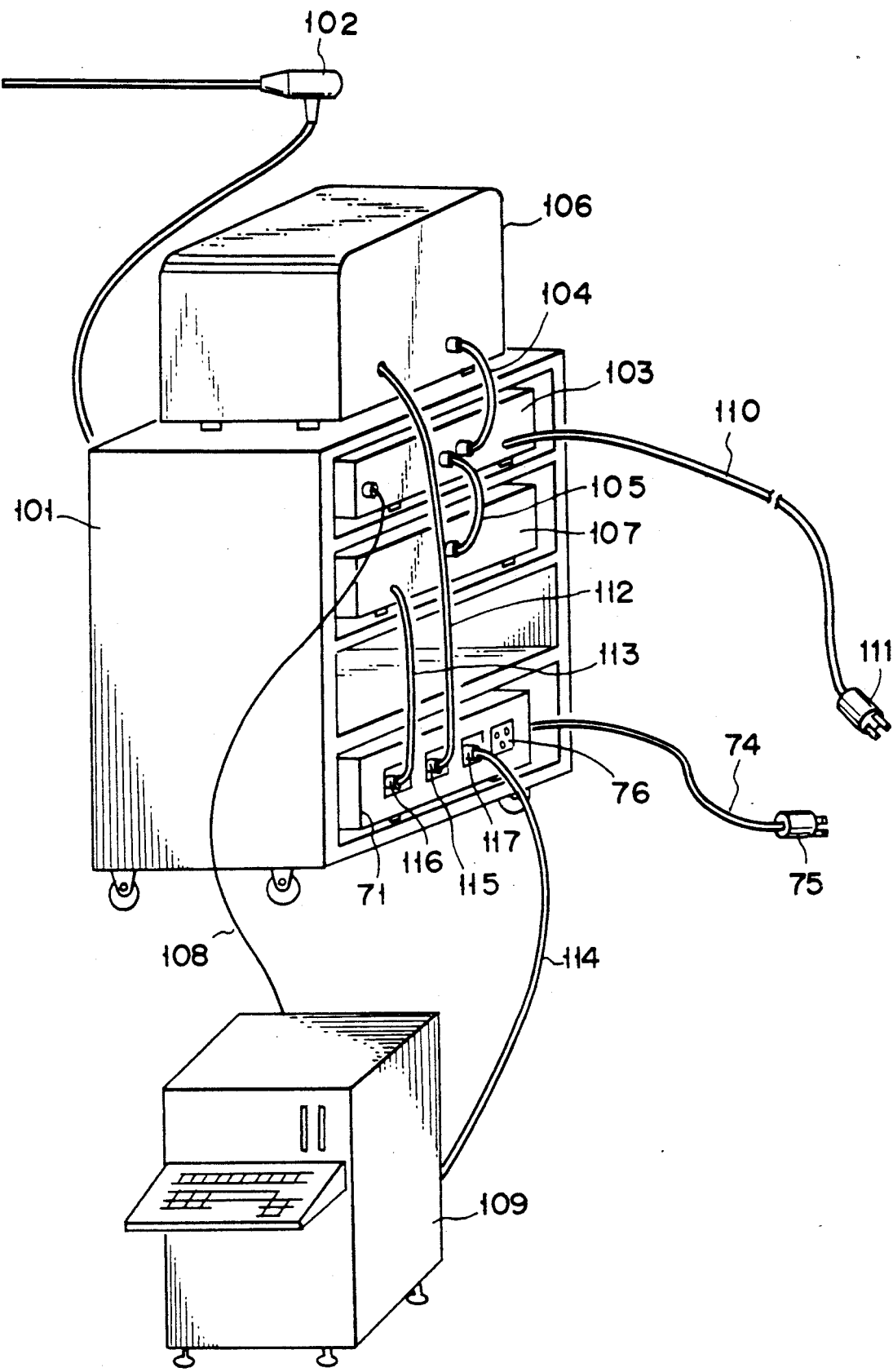
FIG. 19 is a perspective view showing a fifth embodiment of the present invention.

FIG. 19 shows a fifth embodiment of the present invention. In the fifth embodiment, the present invention is applied to an electronic endoscope system mounted on a cart 101. An electronic endoscope 102 is connected to an imaging apparatus (ME device) 103 having a light source device therein. An image output signal from the imaging apparatus 103 is supplied through signal lines 104 and 105 to a TV monitor 106 and a video tape recorder 107. The imaging apparatus 103 is connected to a computer apparatus 109 through a signal line 108. Image data supplied from the imaging apparatus through the signal line 108 is stored and/or processed in the computer apparatus 109. The computer apparatus 109 is connected to the TV monitor 106 through a signal line, and processed image signals are sent to the TV monitor 106.

The ME device or the imaging apparatus 103 has a power source cord 110. A plug 111 is coupled to an end portion of the cord 110. The plug 111 is connected to a wall socket (a socket for medical use connected to a commercial power source).

Power supply plugs 115, 116 and 117 coupled to end portions of power source cords 112, 113 and 114 of general electric devices or the TV monitor 106, video tape recorder 107 and computer apparatus 109 are connected to the sockets 76 of the isolating transformer apparatus 71 of the fourth embodiment. The isolating transformer apparatus 71, along with the electronic endoscope 102, imaging apparatus 103, TV monitor 106 and video tape recorder 107, is mounted on the cart 101.

As described above, since the plugs 115, 116 and 117 of the general electric devices or the TV monitor 106, video tape recorder 107 and computer apparatus 109 are connected to the sockets 76 of the isolating transformer apparatus 71, the leakage current of the general electric devices, when combined with the ME device or the imaging apparatus 103, can be reduced to a level of that of the ME device, thus improving safety. Further, once the plugs 115, 116 and 117 are inserted into the sockets 76 to predetermined positions, the operation lever 85 of each socket 76 cannot be touched unless the screws 88 are taken off by means of the disengaging tool K (such as a driver) and the cover 73 is removed from the casing 72. Thus, such a dangerous situation can be prevented from occurring, that a user pulls out the plugs 115, 116 and 117 from the sockets 76 and connects them to the wall socket.

In the fifth embodiment, the present invention has been applied to an electronic endoscope system. Of course, this invention may be applied to an ultrasonic endoscope system.

Figure 20:
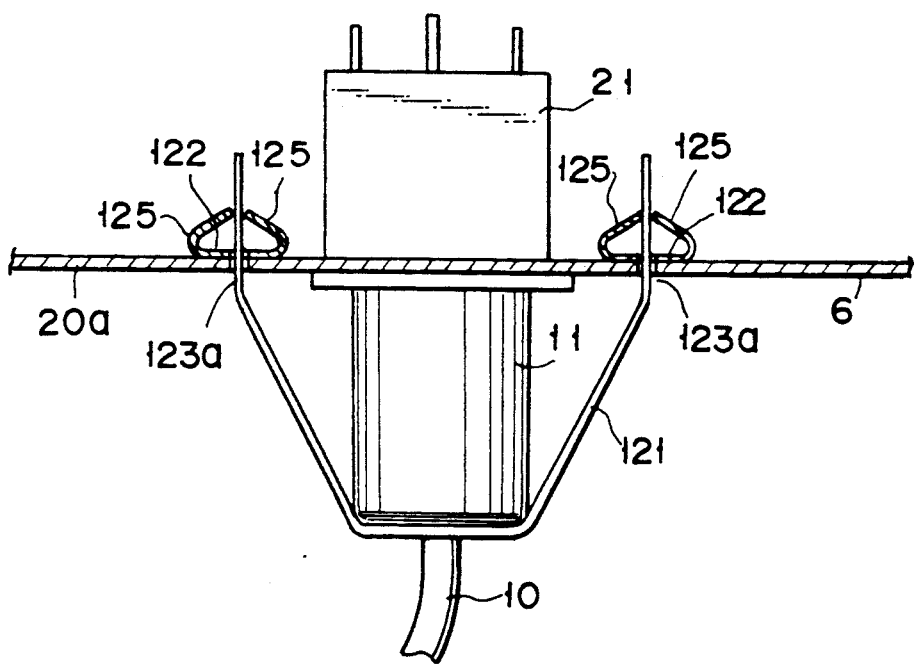
FIG. 20 is a transverse cross-sectional view illustrating the connection between the power source socket and the power source plug according to a sixth embodiment of the present invention.
Figure 21:
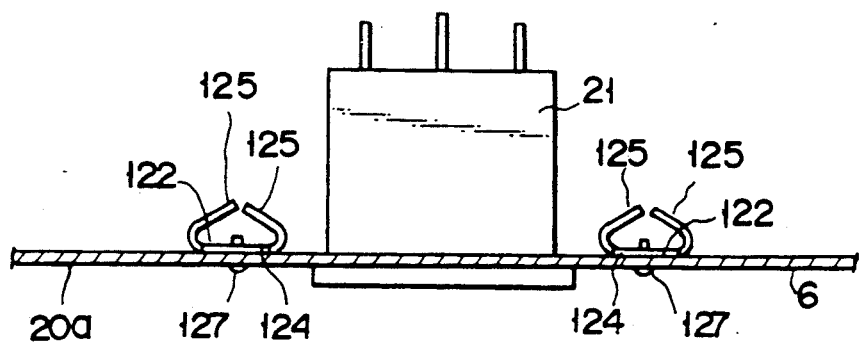
FIG. 21 is a transverse cross-sectional view illustrating the state in which the power source plug is disconnected from the power source socket of FIG. 20.

FIGS. 20 to 25 show a sixth embodiment of the present invention. In the sixth embodiment, the plug 11 or 15 of general electric device 9 or 13, which is connected to the sockets 21 of the isolating transformer apparatus 6 of the first embodiment, is fixed by means of a fixing band (retainer means) 121. Band fixing members (fixing means) 122 for securing the fixing band 121 are arranged on the front panel 20a of casing 20 of isolating transformer apparatus 6. As shown in FIG. 21, the band fixing members 122 are arranged on both sides of each socket 21 and on an inner surface of front panel 20a of casing 20.

A pair of band insertion holes 123a for allowing insertion of both end portions of the fixing band 121, and a pair of insertion holes 123b (see FIG. 26) for allowing insertion of band releasing members 129 (described later), are formed in the front panel 20a of casing 20 on both sides of each sockets 21.

Figure 22:
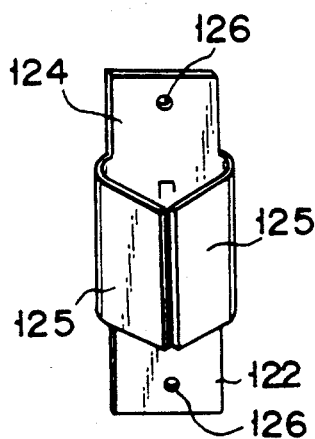
FIG. 22 is a perspective view showing a band stopper of FIG. 20.
Figure 23:
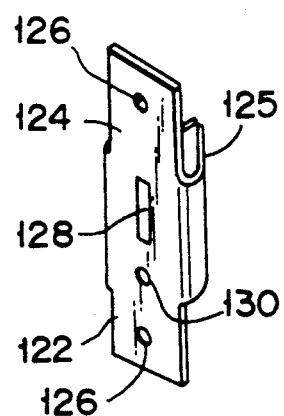
FIG. 23 is a perspective view showing an insertion hole of the band stopper of FIG. 22 into which a band releasing member is inserted.

As shown in FIGS. 22 and 23, each band fixing member 122 includes a fixed plate 124 fixed on the inner surface of the front panel 20a of casing 20, and a pair of spring-like clamp fingers 125 attached to both side edges of the fixed plate 124 and clamping the fixing band 121. Free end portions of fingers 125 are bent toward the inside of the casing 20 and toward each other. When both end portions of the fixing band 121 are inserted into the band insertion holes 123a, the inserted end portion of the fixing band 121 open the clamp fingers 125 against the clamping force of the fingers 125. Once the fixing band 121 is inserted to a predetermined position, the clamp fingers 125 clamp the fixing band 121. In other words, when a force acts on the fixing band 121 in a direction of pull-out of the fixing band 121, the clamping force of fingers 125 acts on the fixing band 121, thus preventing the pull-out of the fixing band 121.

A pair of screw holes 126 are formed in upper and lower portions of the fixed plate 124 of band fixing member 122. Fixing screws 127 are inserted through the screw holes 126 to fix the band fixing member 122 to the front panel 20a of casing 20. Further, the fixed plate 124 has a band insertion hole 128 and an insertion hole 130 for the band releasing member 129 shown in FIG. 25. The band insertion hole 128 and the band releasing member insertion hole 130 of the fixed plate 124 are located so as to correspond to the band insertion hole 123a and the band releasing hole 123b formed in the front panel 20a of casing 20.

The band releasing member 129 comprises a handle portion 129a and an operation pin 129b connected to the handle portion 129a. The outer diameter of the operation pin 129b is greater than the thickness of the fixing band 121. The band releasing member 129 is made of an insulating material.

Figure 24:
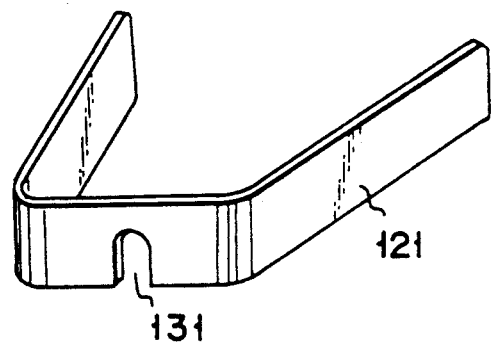
FIG. 24 is a perspective view showing a fixing band of FIG. 20.
Figure 25:
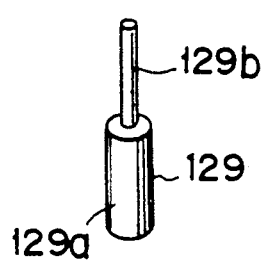
FIG. 25 is a perspective view showing a band releasing member in the sixth embodiment.

As shown in FIG. 24, a U-shaped notch 131 is cut in a substantially middle portion of the fixing band 121. When the fixing band 121 is used, the cord 10 or 14 of the plug 11 or 15 passes through the notch 131.

The operation of the sixth embodiment will now be described.

The plug 11 or 15 of general electric device 9 or 13 is connected to the socket 21 of the insulating transformer apparatus 6. The cord 10 or 14 of the plug 11 or 15 is let to pass through the notch 131 of the fixing band 121. In this state, both end portions of the fixing band 121 are inserted into the band insertion holes 128 of the band fixing member 122 through the band insertion holes 123a of the casing 20. The end portions of the fixing band 121 open the clamp fingers 125 of the band fixing member 122 against the clamping force of the fingers 125. Once the fixing band 121 is inserted to the predetermined position, as shown in FIG. 20, the fingers 125 clamp the fixing band 121.

When the fixing band 121 is to be pulled out of the band fixing member 122, the operation pin 129b of band releasing member 129 is passed through the band releasing member insertion hole 123b in casing 20 and the band releasing member insertion hole 130 in the band fixing member 122. Thus, the operation pin 129b is inserted between the clamp fingers 125 of band fixing member 122. Since the outer diameter of the operation pin 129b is greater than the thickness of the fixing band 121, the clamp fingers 125 of band fixing member 121 are opened by the operation pin 129b by a distance greater than the thickness of the fixing band 121. If the fixing band 121 is pulled out from the casing 2 in this state, the fixing band 121 can be easily removed from the band fixing member 122.

In the above-described sixth embodiment, after the plug 11 or 15 of electric device 9 or 13 is connected to the sockets 21 of the isolating transformer apparatus 6, both end portions of the fixing band 121 are inserted between the clamp fingers 125 through the band insertion holes 123a in casing 20 and the band insertion holes 128 in ban fixing member 122. In this state, the fixing band 121 is held by the clamping force of the fingers 125. The fixing band 121 cannot be removed from the band fixing member 122, unless the operation pin 129b of band releasing member 129 is inserted into the band releasing member insertion hole 130 in band fixing member 122 through the band releasing member insertion hole 123b in casing 20. Thus, the user is prohibited from pulling out the plug 11 or 15 and connecting it to the wall socket. Thus, a danger of electric shock can be surely avoided, and safety can be ensured.

Figure 26:
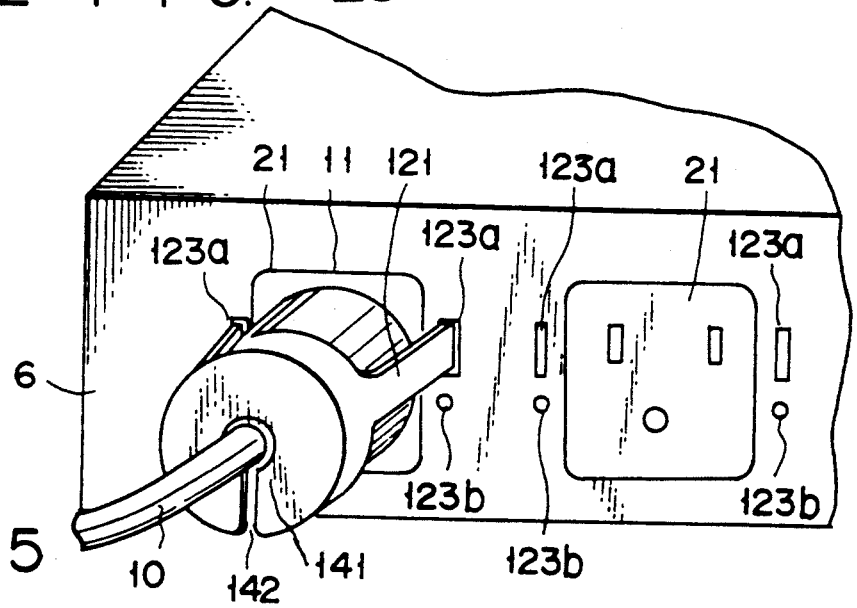
FIG. 26 is a perspective view illustrating the connection between the power source socket and the power source plug according to a seventh embodiment of the present invention.
Figure 27:
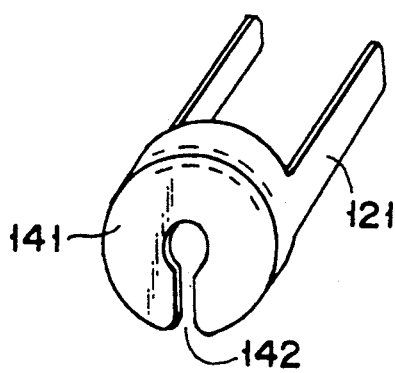
FIG. 27 is a perspective view showing a fixing band in the seventh embodiment.

FIGS. 26 and 27 show a seventh embodiment of the present invention. In the seventh embodiment, a plug holder 141 of a substantially cylindrical shape for holding the cord 10 or 14 of the plug 11 or 15 of electric device 9 or 13 is provided at a middle region of the fixing band 121 of the sixth embodiment. The plug holder 141 has a U-shaped notch 142. When the fixing band 121 is used, the cord 10 or 14 of the plug 11 or 15 is passed through the notch 142.

In the seventh embodiment, when the fixing band 121 is mounted on the plug 11 or 15 of electric device 9 or 13, the fixing band is easily removed from the plug 11, and the removal of the plug 11 or 15 can be prevented.

Figure 28:
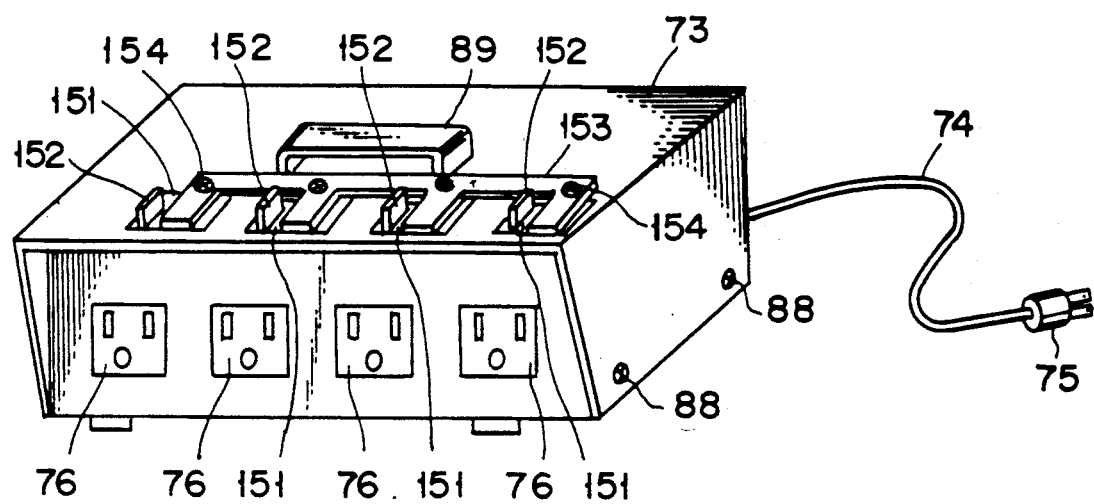
FIG. 28 is a perspective view showing a eighth embodiment of the invention.

FIG. 28 shows an eighth embodiment of the present invention, wherein operation lever insertion holes 151 are formed in the upper face of the cover 73 of casing 72 of the fourth embodiment. The operation lever 85 of socket 76 has an upwardly extended portion 152 The extended portion 152 is projected from the operation lever insertion hole 151 in the upper face of the cover 73. This structure allows the user to operate the lever 85 without removing the cover 73 from the casing 72. A locking plate 152 is attached on the upper face of the cover 73 by means of screws 154. The locking plate 153 restricts and prohibits the movement of the extended portion 152 of lever 85.

In this case, unless the locking plate 153 is removed from the cover 73 by disengaging the screws 154 by means of a disengaging tool K like a driver, the user is not allowed to operate the extended portion 152 of lever 85 of socket 76. Once the plug 11 or 15 is connected to the socket 76, the user is prevented from pulling out the plug 11 or 15 and connecting it to the wall socket. Thus, a danger of electric shock due to leakage current from the electric device 9 or 13 can be surely avoided, and safety can be ensured.

The present invention is not limited to the above embodiments, and various changes or modifications can be made to this invention within the scope of the claims.

What is claimed is:

1. A medical apparatus comprising the combination of:

an electrical medical apparatus for use with an endoscope connectable thereto and adapted for at least one of a diagnostic and medical treatment;

at least one electrical non-medical apparatus including a line cord and a plug, said at least one electrical non-medical apparatus being used in association with said electrical medical apparatus; and an isolating transformer apparatus isolating a patient from electrical shocks from said electrical medical apparatus used together with said electrical non-medical apparatus, said isolating transformer apparatus being connectable by an authorized person to a commercial power supply and being connected to said line cord and plug of said electrical non-medical apparatus, said electrical medical apparatus being connectable to said commercial power supply, said isolating transformer apparatus including:

a housing having a plurality of walls;

a transformer contained in said housing, said transformer having a primary and secondary winding, said primary winding being connectable to said commercial power supply, and said secondary winding being electrically isolated from said primary winding;

a power supply socket mounted on said wall of said housing and being connected to said secondary winding, said socket having means for receiving therein said plug of said electrical non-medical apparatus;

retainer means provided on an outside portion of said housing, said retainer means preventing said plug of said electrical non-medical apparatus from being removed when said plug is connected to said power supply socket; and locking means for locking said retainer means to said housing, said locking means preventing removal of said retainer means without an engaging and disengaging tool.

2. The medical apparatus according to claim 1 wherein said retainer means includes a notch which is dimensioned such that said line cord of the at least one non-medical apparatus can fit in the notch, and said line plug is too large to fit through the notch.

3. The medical apparatus according to claim 2, wherein said locking means includes at least one screw for attaching said retainer means to said housing.

4. The medical according to claim 1, wherein retainer means are provided and mounted over said plug to inhibit removal of said plug and wherein said locking means locks said retainer means to said housing so as to prevent removal of said plug.

5. The medical apparatus according to claim 4, wherein said housing has an L-shaped plate fixed thereto in a region near said socket; and said retainer means comprises a notched retainer attached to said L-shaped attaching plate, said notch being dimensioned such that said line cord can fit therethrough and said plug is too large to fit therethrough.

6. The medical apparatus according to claim 4, wherein said retainer means includes a box-shaped retainer covering the periphery of said line plug when said plug is connected to said socket, the box-shaped retainer including a notch for said line cord to pass therethrough.

7. The medical apparatus according to claim 4, wherein said retainer means includes a holding belt having two end portions for holding said power source plug, both said end portions of the holding belt being inserted into said housing, and said locking means includes belt attachment means, provided on said housing for holding both of said end portions of said holding belt.

8. The medical apparatus according to claim 7, wherein said belt attachment means is fixed inside said housing and comprises:

a clamp having a pair of elastic clamp fingers for clamping both end portions of said holding belt, said fingers extending toward the inside of the housing and toward each other; and an aperture having a size greater than the thickness of said holding belt, and wherein a unique disengaging tool is provided for said locking means, said tool comprising a pin inserted to said aperture in the wall of the housing, the outer diameter of the pin being substantially equal to the diameter of the aperture.

9. The medical apparatus according to claim 7, wherein said holding belt has a U-shaped notch through which said cord is passed, said notch being dimensioned such that the cord of the plug can be fit through the notch and said plug is too large to fit therethrough.

10. The medical apparatus according to claim 7, wherein said holding belt includes a plug holder for holding the end portion of the plug which is connected to said line cord, the plug holder having a U-shaped notch therein through which the cord of the plug can pass.

11. The medical apparatus according to claim 1, further comprising a movable table on which said housing is mounted, said table including a section for mounting said non-medical electric apparatus thereon.

12. The medical apparatus according to claim 1, wherein said electrical non-medical apparatus comprises at least a recording device and a display device.

13. The medical apparatus according to claim 12, wherein:

said electrical medical apparatus has an image device which is used with the endoscope connected thereto said image device including means for supplying light to the endoscope, and means for outputting an electrical image signal from the endoscope;

said recording device is connected to said image device and stores an image from said image device; and said display device includes means for displaying the image from said image device.

* * * * *

UNITED STATES PATENT AND TRADEMARK OFFICE
CERTIFICATE OF CORRECTION

PATENT NO. : 5,174,293

DATED : December 29, 1992

INVENTOR(S) : Toshihiko HAGIWARA

It is certified that error appears in the above-identified patent and that said Letters Patent is hereby corrected as shown below:

Title page, Section [54], line 1, "ON" should be --AN--.

Signed and Sealed this

Eighth Day of March, 1994

Attest:

BRUCE LEHMAN

*Attesting Officer*    *Commissioner of Patents and Trademarks*